(12) United States Patent
Stopek

(10) Patent No.: US 8,153,741 B2
(45) Date of Patent: *Apr. 10, 2012

(54) FURANONE COPOLYMERS

(75) Inventor: Joshua B. Stopek, Yalesville, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/190,927

(22) Filed: Jul. 26, 2011

(65) Prior Publication Data

US 2011/0280824 A1     Nov. 17, 2011

Related U.S. Application Data

(63) Continuation of application No. 12/594,618, filed as application No. PCT/US2008/063149 on May 9, 2008, now Pat. No. 7,999,051.

(60) Provisional application No. 60/930,108, filed on May 14, 2007.

(51) Int. Cl.
    *C08F 224/00*     (2006.01)

(52) U.S. Cl. ........ 526/270; 514/114; 514/473; 514/613; 514/645; 424/422; 424/423; 424/427; 424/443

(58) Field of Classification Search .................. 526/270; 514/114, 473, 613, 645; 424/422, 423, 427, 424/443
See application file for complete search history.

(56) References Cited

U.S. PATENT DOCUMENTS

| | | | | |
|---|---|---|---|---|
| 7,999,051 | B2 * | 8/2011 | Stopek ........................ | 526/270 |
| 2003/0157193 | A1 | 8/2003 | McDonald et al. | |
| 2008/0033106 | A1 | 2/2008 | Koroskenyi et al. | |
| 2010/0076489 | A1 * | 3/2010 | Stopek et al. .................. | 606/232 |
| 2010/0087840 | A1 * | 4/2010 | Ebersole et al. ............... | 606/151 |

FOREIGN PATENT DOCUMENTS

| | | |
|---|---|---|
| WO | WO 99/54323 A1 | 10/1999 |
| WO | WO 01/76594 A1 | 10/2001 |
| WO | WO 02/00639 A1 | 1/2002 |
| WO | WO 03/084322 A2 | 10/2003 |
| WO | WO 2005/053684 A1 | 6/2005 |
| WO | WO 2007/085042 A1 | 8/2007 |
| WO | WO 2007/133777 A1 | 11/2007 |
| WO | WO 2007/133781 A2 | 11/2007 |
| WO | WO 2007/133782 A1 | 11/2007 |

OTHER PUBLICATIONS

International Search Report for PCT/US08/063149 date of completion is Aug. 5, 2008 (2 pages).

Iwasaki et al. In vitro and ex vivo blood compatibility study of 2-methacryloyloxyethyl phosphorylcholine (MPC) copolymer-coated hemodialysis hollow fibers. The Japanese Society for Artificial Organs 2003, 6(4):260-266; p. 261 and 266.

Nakabayashi et al. Copolymers of 2-rnethacryloyloxyethyl phosphorylcholine (MPC) as biomaterials. Bio-Medical Materials and Engineering 2004, vol. 14. p. 345-354.

Baveja, J.K., et al. "Biological performance of a novel synthetic furanone-based antimicrobial", *Biomaterials*, vol. 25, pp. 5013-5021 (2004).

Al-Bataineh, Sameer A., et al., "XPS characterization of the surface immobilization of antibacterial furanones", *Surface Science*, vol. 600, pp. 952-962 (2006).

European Search Report From EP Application No. 08 76 9360 mailed Nov. 2, 2010.

Yasuhiko Waasaki and Kazuhiko Ishihara, "Phosphorylcholine-Containing Polymers for Biomedical Applications" Analytical and Bioanalytical Chemistry, vol. 381, pp. 534-546, Nov. 11, 2004.

European Search Report for corresponding EP 08 76 9362, date of completion is Oct. 19, 2010. (3 pages).

\* cited by examiner

*Primary Examiner* — Robert D. Harlan

(57) ABSTRACT

The present disclosure provides copolymers including a first monomer including at least one phospholipid possessing at least one vinyl group and a second monomer including a furanone possessing vinyl and/or acrylate groups. Compositions, medical devices, and coatings including such copolymers are also provided.

18 Claims, No Drawings

FURANONE COPOLYMERS

CROSS-REFERENCE TO RELATED APPLICATIONS

This application is a continuation of U.S. application Ser. No. 12/594,618 filed Oct. 5, 2009 now U.S. Pat. No. 7,999,051, which is a National Stage Application of PCT/US2008/063149 under 35USC §371 (a) filed May 9, 2008, which claims priority of U.S. Provisional Patent Application Ser. No. 60/930,108 filed May 14, 2007, the disclosures of each of the above-identified applications are hereby incorporated by reference in their entirety.

TECHNICAL FIELD

The present disclosure relates to furanone copolymers, compositions containing such copolymers, and articles made from or coated with such copolymers or compositions.

BACKGROUND OF RELATED ART

Antimicrobial agents have been used within and/or on medical devices such as intraocular lenses, contact lenses, sutures, meshes, packages containing such devices, and the like. However, some medical devices may not provide effective levels of antimicrobial activity for a sufficient period of time. Moreover, antimicrobial agents on medical devices can be undesirably transferred to their packages, requiring the use of higher levels of antimicrobial agents in order to obtain the desired antimicrobial effect upon implantation or use of the medical devices in vivo.

Accordingly, there is a need for medical devices, packaging materials and textiles that can retain enhanced antimicrobial efficacy.

SUMMARY

The present disclosure provides copolymers possessing a first monomer including at least one vinyl phospholipid monomer, and a second monomer of formula:

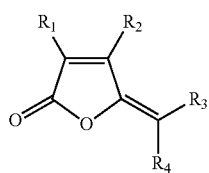

wherein $R_2$, $R_3$ and $R_4$ are independently or all H or halogen;

$R_1$ is a moiety such as H, halogen, formyl, carboxyl, cyano, ester, amide, alkyl, alkoxy, oxoalkyl, alkenyl, alkynyl, aryl or arylalkyl; and at least one of $R_1$, $R_2$, $R_3$ and $R_4$ are substituted with a moiety such as vinyl moieties and/or acrylate moieties.

In embodiments, a copolymer of the present disclosure may include a first monomer comprising a phosphorylcholine possessing at least one vinyl group of the formula:

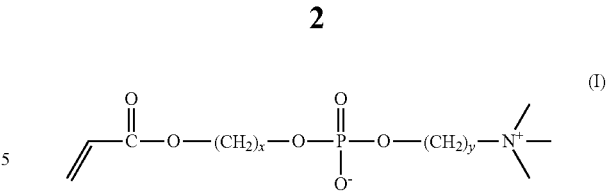

wherein x is from about 1 to about 10 and y is from about 1 to about 10, and a furanone monomer of formula:

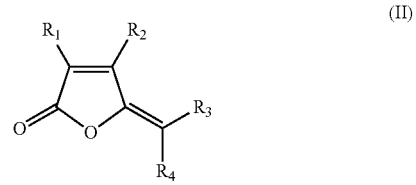

wherein $R_2$, $R_3$ and $R_4$ are independently or all H or halogen; and $R_1$ is a moiety such as H, halogen, formyl, carboxyl, cyano, ester, amide, alkyl, alkoxy, oxoalkyl, alkenyl, alkynyl, aryl or arylalkyl, wherein at least one of $R_1$, $R_2$, $R_3$ and $R_4$ are substituted with a moiety such as vinyl moieties and/or acrylate moieties.

Compositions including a copolymer of the present disclosure are also described. Articles made from, or coated with, a copolymer of the present disclosure or a composition including a copolymer of the present disclosure, are also described.

Copolymers and/or compositions of the present disclosure provide an easy and inexpensive method of incorporating or applying antimicrobial agents to a medical device, packaging material or textile that provides protection against microorganisms for extended periods of time, with minimal loss of the antimicrobial agents from the article and/or minimal transference of the antimicrobial agent to packaging materials, and the like. In this way, lower amounts of antimicrobial agents may be utilized to achieve the desired antimicrobial effect.

DETAILED DESCRIPTION

The present disclosure provides copolymers including at least one vinyl phospholipid monomer and at least one furanone, and compositions including such copolymers.

The present furanone copolymers may be bioabsorbable or nonabsorbable. As used herein the term "copolymer" includes, but is not limited to, random, block, graft and/or segmented copolymers.

Copolymers of the present disclosure may possess, as a first monomer, at least one phospholipid possessing at least one vinyl group. Such phospholipids are within the purview of those skilled in the art and include, for example, vinyl functional phosphorylcholine monomers, such as 2-methacryloyloxyethyl phosphorylcholine (MPC), 2-acryloyloxyethyl phosphorylcholine, and the like, and combinations thereof. Other phosphorylcholines may be utilized, including phosphorylcholines based upon, or derived from, monomers including, but not limited to, 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butylphosphate, and combinations thereof. As used herein, "(meth)acryl" includes both methacryl and/or acryl groups. Methods for forming phosphorylcholines from such monomers are within the purview of those skilled in the art.

In embodiments, suitable vinyl phosphorylcholines may be of the following formula:

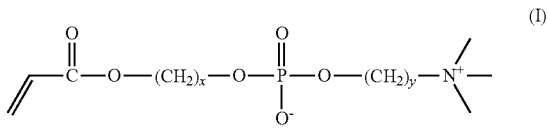

wherein x is from about 1 to about 10, in embodiments from about 2 to about 6, and y is from about 1 to about 10, in embodiments from about 2 to about 6.

In embodiments, suitable phosphorylcholines include those commercially available as PC 1059, PC 1036, PC 1062, PC 2028, PC 1071, PC 1015, and/or PC 2083 from Biocompatibles Limited (Middlesex, UK).

The copolymers of the present disclosure may be formed by polymerizing the above phospholipid possessing at least one vinyl group with a furanone possessing vinyl and/or acrylate groups. Suitable furanones possessing vinyl and/or acrylate groups for use in forming the copolymers in accordance with the present disclosure include, for example, compounds of formula:

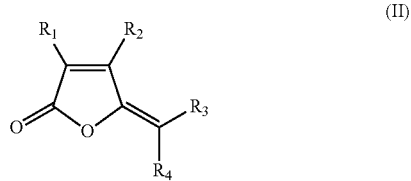

wherein $R_2$, $R_3$ and $R_4$ are independently or all H or halogen; and $R_1$ is a moiety such as H, halogen, acrylate, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic, and/or fluorophilic; with the proviso that at least one of $R_1$, $R_2$, $R_3$ and $R_4$ are substituted with a vinyl moiety and/or an acrylate moiety. In embodiments, the furanone possessing vinyl and/or acrylate groups may also be halogenated.

As used herein, "halogen" and/or "halogenated" includes fluorine, chlorine, bromine or iodine.

As used herein, a substituted furanone or substituted moiety includes one possessing a group such as alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenylacyl, alkynylacyl, acylamino, diacylamino, acyloxy, alkylsulfonyloxy, heterocyclyl, heterocycloxy, heterocyclamino, haloheterocyclyl, alkylsulfenyl, carboalkoxy, alkylthio, acylthio, phosphorus-containing groups such as phosphono and phosphinyl, and combinations thereof.

As used herein, "alkyl", used either alone or in compound words such as "haloalkyl" or "alkylthio", includes straight chain or branched $C_{1-12}$ alkyl groups. Examples include methyl, ethyl, propyl, isopropyl and the like.

As used herein, "alkoxy" includes straight chain or branched alkoxy, in embodiments $C_{1-12}$ alkoxy such as methoxy, ethoxy, n-propoxy, isopropoxy and butoxy isomers.

As used herein, "alkenyl" includes groups formed from straight chain, branched or mono- or polycyclic alkenes including ethylenically mono- or poly-unsaturated alkyl or cycloalkyl groups as previously defined, in embodiments $C_{2-12}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, and/or 1,3,5,7-cyclooctatetraenyl.

As used herein, "heteroatoms" include O, N and/or S.

As used herein, "acyl" used either alone or in compound words such as "acyloxy", "acylthio", "acylamino" or "diacylamino" includes carbamoyl, aliphatic acyl groups and acyl groups containing a heterocyclic ring which may be referred to as heterocyclic acyl, in embodiments $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopopylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; and/or heterocyclylglyoxyloyl, such as thiazolidinylglyoxyloyl or pyrrolidinylglyoxyloyl.

As used herein, "fluorophilic" includes the highly attractive interactions certain groups, such as highly fluorinated alkyl groups of $C_4$-$C_{10}$ chain length, have for perfluoroalkanes and perfluoroalkane polymers.

In other embodiments, a suitable furanone may be of the following formula:

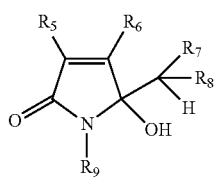
(III)

wherein $R_5$ and $R_6$ are independently H, halogen, hydroxy, substituted or unsubstituted alkyl, substituted or unsubstituted alkoxy, substituted or unsubstituted oxoalkyl, substituted or unsubstituted alkenyl, substituted or unsubstituted aryl, or substituted or unsubstituted arylalkyl, optionally interrupted by one or more hetero atoms, straight chain or branched chain, hydrophilic or fluorophilic, $R_7$ and $R_8$ are independently H, halogen, substituted or unsubstituted alkyl, substituted or unsubstituted alkoxy, substituted or unsubstituted aryl, or substituted or unsubstituted arylalkyl, and $R_9$ is H, hydroxy, substituted or unsubstituted alkyl, substituted or unsubstituted alkoxy, substituted or unsubstituted oxoalkyl, substituted or unsubstituted alkenyl, substituted or unsubstituted aryl or substituted or unsubstituted arylalkyl, optionally interrupted by one or more hetero atoms, straight chain or branched chain, hydrophilic or fluorophilic.

Specific examples of such compounds of formula III include, for example, the following:

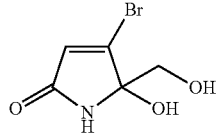
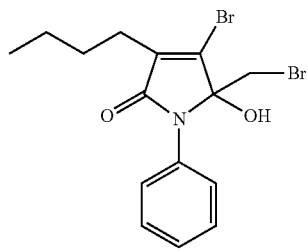
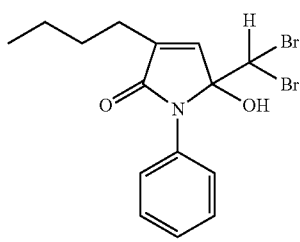
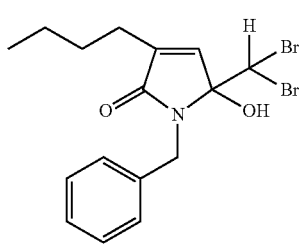

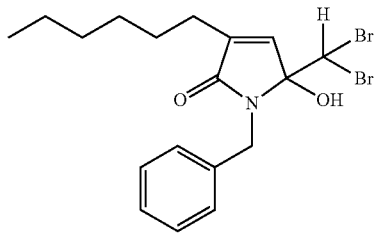
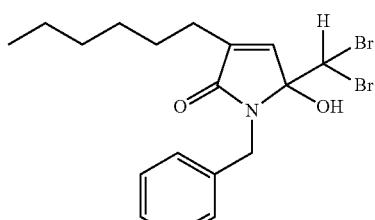
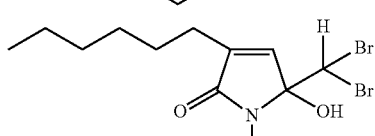
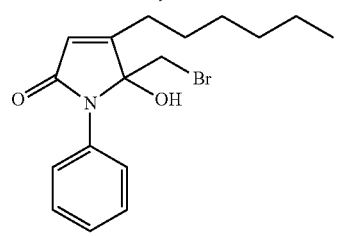
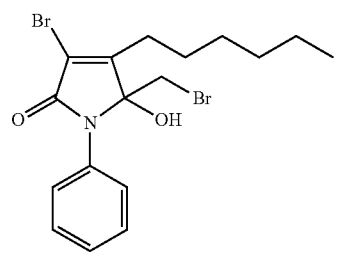

In some embodiments, the above furanones of formula III may be dehydrated to form another suitable furanone compound of the following formula IV:

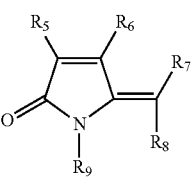
(IV)

wherein $R_5$, $R_6$, $R_7$, $R_8$, and $R_9$ are as defined above.

Specific examples of compounds of formula IV include the following:

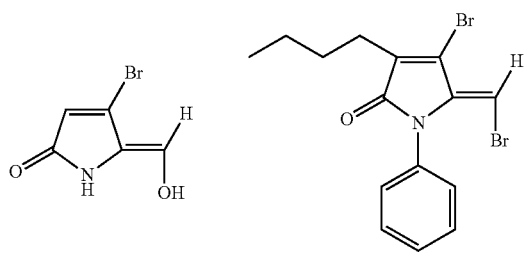
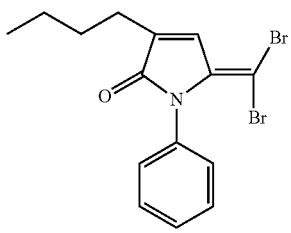
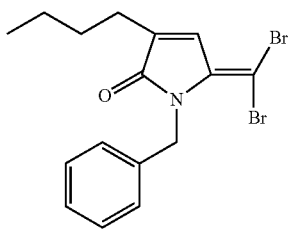
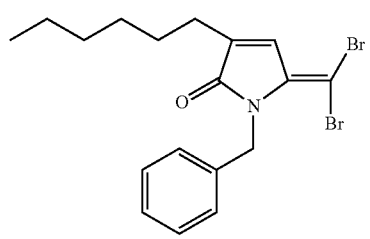
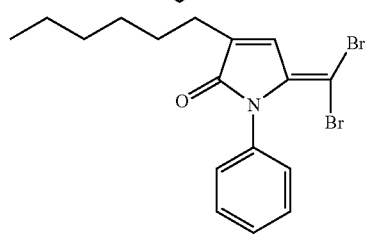
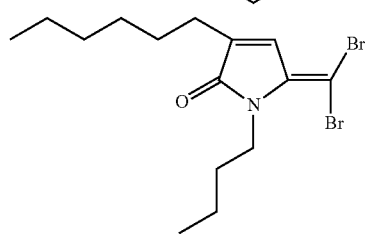
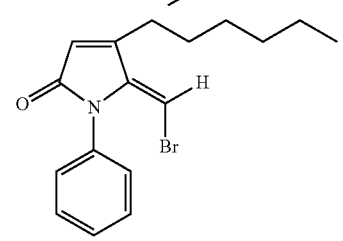
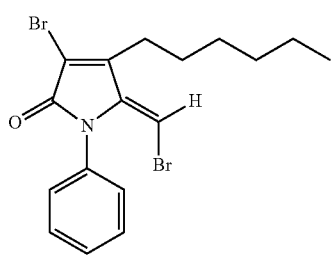
Other suitable furanone derivatives may include, in embodiments, those of the following formula:
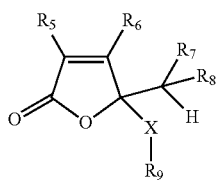
wherein $R_5$, $R_6$, $R_7$, $R_8$ and $R_9$ are as defined above and X is O or $NR_5$.
Specific examples of furanones of formula V include, but are not limited to, the following:
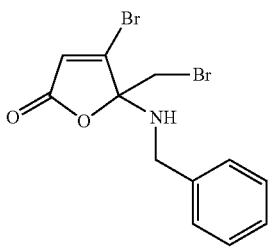
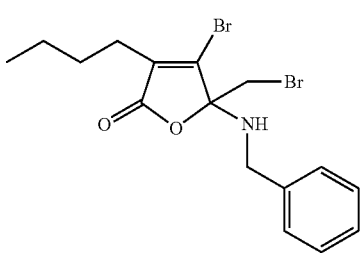
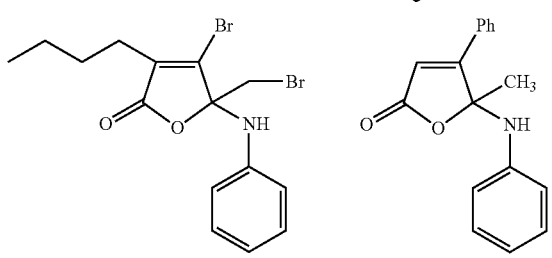

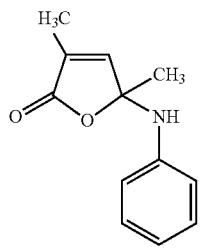 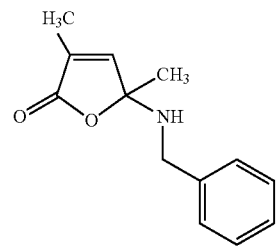

Yet other suitable furanones include those of the following formula:

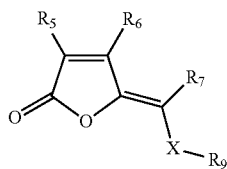
(VI)

wherein $R_5$, $R_6$, $R_7$ and $R_9$ are as defined above, and X is O or $NR_5$.

Specific examples of furanones of formula VI include, but are not limited to, the following:

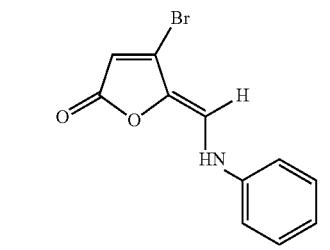

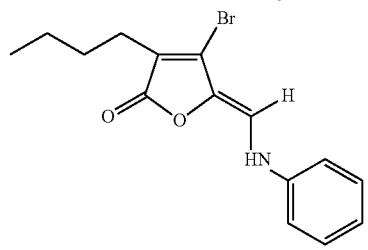

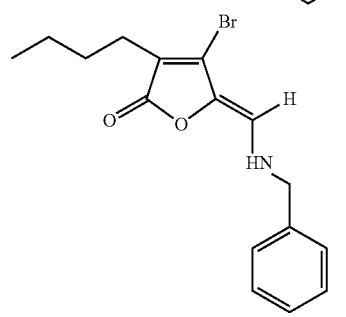

Yet other suitable furanones include those of the following formula:

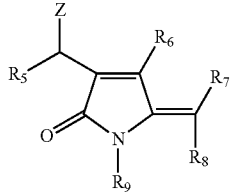
(VII)

wherein $R_5$, $R_6$, $R_7$, $R_8$ and $R_9$ are as defined above, and Z is $R_6$, halogen, $OC(O)R_6$, =O, amine, azide, thiol, mercaptoaryl, arylalkoxy, mercaptoarylalkyl, $SC(O)R_6$, $OS(O)_2R_6$, $NHC(O)R_6$, =$NR_6$, or $NHR_6$.

Specific examples of compounds of formula VII include, but are not limited to, the following:

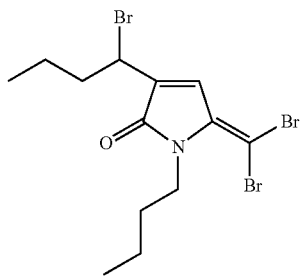

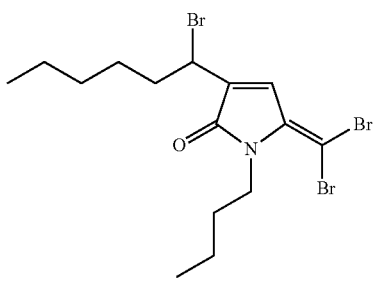

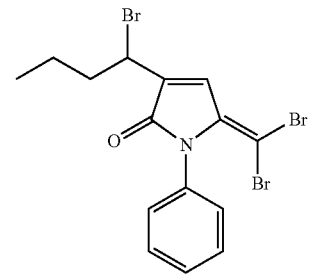

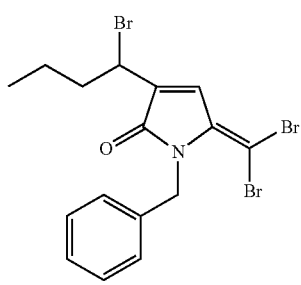

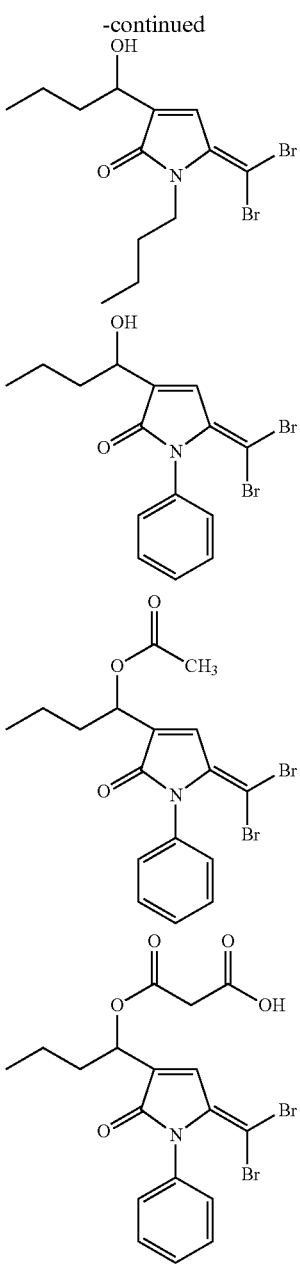

Conditions for conducting the copolymerization of the above furanones with the at least one phospholipid possessing at least one vinyl group are within the purview of those skilled in the art. The copolymerization can be achieved by reacting the at least one phospholipid possessing at least one vinyl group with a furanone possessing a vinyl and/or acrylate group. The conditions under which the at least one phospholipid possessing at least one vinyl group may be reacted with the furanone may vary widely depending on the specific phospholipid, the specific furanone being employed, and the desired degree of polymerization to be achieved. The molar ratio of phospholipid to furanone may be from about 1:10 to about 10:1. In embodiments, the amount of furanone employed can be from about 2 to about 8 moles of furanone per mole of phospholipid possessing at least one vinyl group. Suitable reaction times and temperatures can be from about 15 minutes to about 72 hours, in embodiments from about 60 minutes to about 24 hours, at temperatures of from about 0° C. to about 250° C., in embodiments from about 25° C. to about 80° C.

In embodiments, the copolymers of the present disclosure may be prepared from monomer solutions prepared by dissolving the furanone possessing vinyl or acrylate groups in a liquid vinyl monomer or monomer solution, for example the at least one phospholipid possessing at least one vinyl group. Suitable solvents which may be utilized in forming such solutions include, for example, water, lower alcohols, mixtures of the foregoing, and the like. In other embodiments, an aqueous solution or suspension may be formed with the furanone possessing vinyl and/or acrylate groups in combination with the at least one phospholipid possessing at least one vinyl group. In yet other embodiments, the furanone possessing vinyl or acrylate groups may be combined with an organic solvent and the resulting solution may then be mixed or emulsified with an aqueous compatible or incompatible solution containing the at least one phospholipid possessing at least one vinyl group. Suitable organic solvents include, for example, ethanol, methanol, isopropanol, chloroform, methylene chloride, combinations thereof, and the like.

In addition to preparing the copolymers of the present disclosure, these methods may also be utilized, in embodiments, for surface/bulk modification of devices by impregnating a device such as a medical device with monomer solutions of the vinyl phospholipid and/or furanone possessing vinyl and/or acrylate groups, for example by immersion, and in situ polymerizing the monomer solutions to prepare graft copolymers or an interpenetrating network of the copolymers of the present disclosure in combination with the device.

Solutions may also be used with chemical couplers, for example silanes, vinyl siloxanes, and the like, to not only graft or interpenetrate the surface of a medical device, but to also covalently tether the copolymers of the present disclosure to the surface of a device.

Polymerization may also be initiated by subjecting the monomers, for example, the furanone possessing vinyl and/or acrylate groups and the at least one phospholipid possessing at least one vinyl group, to energy including irradiation, such as high energy radiation including gamma and/or e-beam, ultraviolet light, pulse laser ablation deposition, plasma energy treatment, chemical initiation, photoinitiation, and the like. In embodiments, the use of high energy radiation initiation may be beneficial as it should not require the use of an additional initiator such as a chemical initiator or catalyst.

The copolymer of the present disclosure may possess the vinyl phospholipid in amounts of from about 5 to about 95 percent by weight of the copolymer, in embodiments from about 15 to about 85 percent by weight of the copolymer. Thus, the copolymer of the present disclosure may possess the furanone possessing vinyl and/or acrylate groups in amounts of from about 5 to about 95 percent by weight of the copolymer, in embodiments from about 15 to about 85 percent by weight of the copolymer.

In embodiments, the phospholipid possessing at least one vinyl group and the furanone possessing vinyl and/or acrylate groups, and optional halogen and/or hydroxyl groups, may also be copolymerized in the presence of additional vinyl or acrylate monomers to obtain copolymers possessing excellent solubility, wettability, thermal properties, film-forming properties, and the like. Such additional vinyl or acrylate monomers may include, for example, vinyl functional quaternary amines, hydroxyethyl methacrylate, n-vinyl pyrrolidone, sodium acrylate, bis-acrylate, styrene sulfonic acid, butyl acrylate, sulfopropyl acrylate, sulfopropyl methacylate, acrylamide, diacrylamide, methacrylic acid, acrylic acid, polyethylene glycol acrylates, polyethylene glycol/polypropylene glycol acrylates, silicone acrylates, combinations thereof, and the like. In addition to forming copolymers with the phospholipid possessing at least one vinyl group and the furanone possessing vinyl and/or acrylate groups, in some embodiments these additional vinyl or acrylate monomers may be combined with the copolymers of the present disclosure as a mixture or blend.

For example, in some embodiments a copolymer of the present disclosure may include a random copolymer of the phospholipid possessing at least one vinyl group, the furanone possessing vinyl and/or acrylate groups, and the additional vinyl or acrylate monomer.

As noted above, in embodiments the furanone possessing vinyl or acrylate groups and the at least one phospholipid possessing at least one vinyl group may be placed into a solution with an additional acrylate or vinyl compound. For example, in some embodiments, a furanone acrylate and MPC may be placed into solution with hydroxyethyl methacrylate (HEMA) (at a ratio of about 50 to about 25 to about 25) and polymerized by subjecting the monomers to gamma radiation to produce a poly(HEMA)-furanone-MPC copolymer. The resulting copolymer may, in embodiments, be in the form of a hydrogel.

Furanones, including halogenated furanones and/or hydroxyl furanones, are known as inhibitors of quorum sensing. Quorum sensing, also known as bacterial signaling, is recognized as a general mechanism for gene regulation in many bacteria, and it allows bacteria to perform in unison such activities as bioluminescence, swarming, biofilm formation, production of proteolytic enzymes, synthesis of antibiotics, development of genetic competence, plasmid conjugal transfer, and spoliation. Quorum sensing is a universal regulatory mechanism used by both Gram-positive bacteria such as *Staphylococcus aureus, Streptococcus pneumoniae, Salmonella enteritidis, Staphylococcus epidermidis, Bacillus subtilis*, and the like, and Gram-negative bacteria such as *Pseudomonas aeruginosa, Escherichia coli, Aeromonas hydrophila*, and the like.

Furanones, including halogenated and/or hydroxyl furanones, may also block quorum sensing and inhibit the growth of bacteria in amounts that are non-toxic to mammalian cells. Given their mechanism of action, furanones' antipathogenic properties may be effective against a broad spectrum of infectious agents and may be able to reduce and/or prevent colonization of both gram positive and gram negative bacteria, including those noted above.

In addition, unlike antibiotics and antiseptic compounds which kill microbes and carry the risk of inducing antimicrobial resistance, furanones, including halogenated and/or hydroxyl furanones, do not exert such evolutionary pressures. Thus, antimicrobial resistance to an article made with or coated with a copolymer of the present disclosure is not a concern.

In accordance with the present disclosure, a quorum sensing inhibitor, such as the furanones possessing a vinyl and/or acrylate group described herein, in embodiments also possessing halogen and/or hydroxyl groups, may act as an antimicrobial agent by inhibiting microbial development and proliferation. In embodiments, a quorum sensing inhibitor may inhibit swarming motility and biofilm formation, both of which frequently underlie the pathophysiology of infectious diseases. The inhibition of swarming and biofilm formation may thus reduce bacterial burden and hence prevent infection and disease progression.

In embodiments, articles prepared from or coated with a copolymer of the present disclosure possessing a furanone, or a composition containing a furanone copolymer of the present disclosure, may thus display improved resistance to bacteria.

The copolymers of the present disclosure may find many uses in the formation of medical devices and coatings thereon. In embodiments, surgical articles can be manufactured from the furanone copolymers described herein. Suitable medical devices include, but are not limited to, clips and other fasteners, staples, sutures, pins, screws, prosthetic devices, wound dressings, bandages, drug delivery devices, anastomosis rings, surgical blades, contact lenses, intraocular lenses, surgical meshes, stents, stent coatings, grafts, catheters, stent/grafts, knotless wound closures, sealants, adhesives, tissue scaffolds, stapling devices, buttresses, lapbands, orthopedic hardware, pacers, pacemakers, and other implantable devices. Fibers can be made from the furanone copolymers of the present disclosure. In embodiments, fibers made of furanone copolymers of the present disclosure may be knitted or woven with other fibers, either absorbable or non-absorbable fibers, to form textiles. The fibers also can be made into non-woven materials to form fabrics, such as meshes and felts.

The present furanone copolymers can be formed into articles using any technique within the purview of those skilled in the art, such as, for example, extrusion, molding and/or solvent casting. The copolymers can be used alone or blended with other polymers, which may be either absorbable or non-absorbable. Copolymers of the present disclosure combined with other materials may be referred to, in embodiments, as compositions of the present disclosure.

Packaging materials which may formed with the copolymers or compositions of the present disclosure include packaging for products such as medical devices, pharmaceuticals, textiles, consumer goods, foods, and the like.

Furanone copolymers of the present disclosure may also be used to form coatings for articles, including textiles, medical devices, and packaging materials. In embodiments, the coating of the present disclosure can be applied as a solution and the solvent evaporated to leave the coating components, in embodiments, the furanone copolymer of the present disclosure. Suitable solvents which may be utilized in forming the solution include any solvent or combination of solvents suitable for the chosen coating composition. To be suitable, the solvent must (1) be miscible with the coating components including the furanone copolymer, and (2) not appreciably affect the integrity of any material used to form the article being coated, such as a suture. Some examples of suitable solvents include alcohols, ketones, ethers, aldehydes, acetonitrile, acetic acid, methylene chloride, chloroform and water. In embodiments, methylene chloride may be used as a solvent.

Medical devices and packaging materials in accordance with the present disclosure can be sterilized in accordance with techniques within the purview of those skilled in the art.

Preparing a coating solution of the present disclosure may be a relatively simple procedure and can be accomplished by blending, mixing, and the like. In one embodiment, where a furanone copolymer of the present disclosure and a solvent such as methylene chloride are utilized to form the coating solution, the desired amount of furanone copolymer may be placed into a container, followed by the addition of the desired amount of methylene chloride. The two ingredients may then be mixed thoroughly to combine the ingredients.

Any technique within the purview of those skilled in the art may be employed for applying the coating solution or suspension to the article. Suitable techniques include dipping, spraying, wiping and brushing. The article wetted with the coating solution or suspension may be subsequently passed through or held in a drying oven for a time and at a temperature sufficient to vaporize and drive off the solvent.

Medical devices possessing a coating of the present disclosure may be formed of furanone copolymers of the present disclosure. In other embodiments, medical devices can also be formed of absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Suitable nonabsorbable materials which may be utilized to form the medical device include polyolefins, such as polyethylene, polypropylene, copolymers of polyethylene and polypropylene, blends of polyethylene and polypropylene, polyesters such as polyethylene terephthalate, polymides, polyamides, combinations thereof, and the like.

Textiles which may be coated with copolymer coatings of the present disclosure include fibers made of furanone copolymers of the present disclosure, as well as other natural fibers, synthetic fibers, blends of natural fibers, blends of synthetic fibers, and blends of natural fibers with synthetic fibers. Suitable other materials utilized to form textiles include polyesters, polyamides, polyolefins, halogenated polymers, polyester/polyethers, polyurethanes, homopolymers thereof, copolymers thereof, and combinations thereof. Specific examples of suitable materials include polyethylene, polypropylene, polybutylene, polyvinyl chloride, polyethylene terephthalate, nylon 6, and nylon 6,6.

In some embodiments, compositions in accordance with the present disclosure may be formed by combining the furanone copolymers with other additional components. In embodiments, coating compositions containing the furanone copolymers of the present disclosure may be combined with a fatty acid component, such as a fatty acid or a fatty acid salt or a salt of a fatty acid ester. Suitable fatty acids may be saturated or unsaturated, and may include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to about 22 carbon atoms, and mixtures thereof. Fatty acid salts including the calcium, magnesium, barium, aluminum, and zinc salts of stearic, palmitic and oleic acids may be useful in some embodiments of the present disclosure. Some useful salts include commercial "food grade" calcium stearate which contains a mixture of about one-third $C_{16}$ and two-thirds $C_{18}$ fatty acids, with small amounts of the $C_{14}$ and $C_{22}$ fatty acids.

Suitable salts of fatty acid esters which may be included in the compositions of the present disclosure include calcium, magnesium, aluminum, barium, or zinc stearoyl lactylate; calcium, magnesium, aluminum, barium, or zinc palmityl lactylate; and/or calcium, magnesium, aluminum, barium, or zinc oleyl lactylate. In embodiments; calcium stearoyl-2-lactylate (such as the calcium stearoyl-2-lactylate commercially available under the tradename VERV from American Ingredients Co., Kansas City, Mo.) may be utilized. Other fatty acid ester salts which may be utilized include those selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium oleyl lactylate, lithium oleyl lactylate, potassium oleyl lactylate, rubidium oleyl lactylate, cesium oleyl lactylate, and francium oleyl lactylate.

Where utilized, the amount of fatty acid component can be from about 5 percent to about 60 percent by weight of the total composition including the copolymer of the present disclosure. In embodiments, the fatty acid component may be present in an amount from about 15 percent to about 55 percent by weight of the total composition.

In one embodiment, the furanone copolymer can be present in an amount from about 45 to about 60 weight percent of the composition and the fatty acid component, such as a fatty acid salt or a salt of a fatty acid ester, can be present in an amount from about 40 to about 55 weight percent of the composition. In embodiments, the furanone copolymer can be present in an amount from about 50 to about 55 weight percent of the composition and the fatty acid component can be present in an amount from about 45 to about 50 weight percent of the composition.

In embodiments, a fatty acid component as described above, including a calcium stearoyl lactate, may be combined with a copolymer of the present disclosure or included in any coating solution utilized to apply a copolymer of the present disclosure to a medical article, packaging, textile, and the like.

In other embodiments, the furanone copolymers of the present disclosure may be combined with additional polymeric materials, such as oligomers and/or polymers. The additional polymeric materials can be bioabsorbable or nonabsorbable. Bioabsorbable polymers which may be utilized in the composition are within the purview of those skilled in the art and include those containing linkages derived from monomers including, for example, glycolide, lactide, glycolic acid, lactic acid, caprolactone, trimethylene carbonate, dioxanones, dioxepanones, and the like, and homopolymers, copolymers and combinations thereof. Similarly, polyorthoesters, polyhydroxy butyrates, polytyrosine carbonates, polyhydroxy alkanoates, combinations thereof, and the like, may be added. The additional polymeric materials may be blended with or bonded to the furanone copolymers of the present disclosure (e.g., to create a block copolymer).

In embodiments, the furanone copolymers of the present disclosure may be combined with polyalkylene oxides such as polyethylene oxides, polyethylene glycol, polypropylene glycol, copolymers thereof, and the like, including those having acrylate groups such as acrylate PEGs, and/or acrylate PEG/PPG copolymers. Such combinations may include blends or copolymers of the furanone copolymers of the present disclosure with the polyalkylene oxide oligomers and/or polymers and/or other non-toxic surfactants. The resulting composition may thus possess antimicrobial properties due to the presence of the furanone copolymers described above. In other embodiments, the furanone copolymers may be combined with silicone acrylates.

If desired, in addition to the furanone copolymers of the present disclosure, compositions described herein can optionally contain additional components, e.g., dyes, antimicrobial agents, growth factors, anti-inflammatory agents, and the like. The term "antimicrobial agent" as used in the present disclosure includes antibiotics, antiseptics, disinfectants and combinations thereof. In embodiments, the antimicrobial agent may be an antiseptic, such as triclosan or one of the furanones described above.

Classes of antibiotics that can be combined with the furanone copolymers include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam. Other antimicrobials which may be added include, for example, antimicrobial peptides and/or proteins, chemotherapeutic drugs, telomerase inhibitors, other furanones including 5-furanones, mitoxanthone, and the like.

Examples of antiseptics and disinfectants which may be combined with the furanone copolymers include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

In other embodiments, polymer drugs, i.e., polymeric forms of such compounds, for example, polymeric antibiotics, polymeric antiseptics, polymeric non-steroidal anti-inflammatory drugs (NSAIDS), and the like, may be utilized.

The furanone copolymers of the present disclosure may be combined with various optional ingredients, such as stabilizing agents, thickeners, colors, and the like. The optional ingredients may be present in an amount of up to about 10% of the total weight of the compositions formed with furanone copolymers of the present disclosure.

As low amounts of furanones are required in compositions of the present disclosure, existing formulations and manufacturing processes need only minimal modifications to produce the compositions described herein. This ease of formulation and production may reduce both the time and cost necessary to prepare compositions of the present disclosure, compared with adding other antimicrobial agents to existing materials.

In embodiments, as the copolymers of the present disclosure possess antimicrobial properties, they may be useful in forming contact lenses, intraocular lenses, and other medical devices or coatings thereon which might otherwise be known to be subject to a high incidence of infection. For contact lenses and intraocular lenses, the lenses may be incubated with a solution which is a poor solvent for the lens, and which possesses the furanone possessing vinyl or acrylate groups and the at least one phospholipid possessing at least one vinyl group. Incubation of the lens with the solution possessing the monomers will swell the surface of the lens with the monomers. The lens and monomers may then be subjected to low dose radiation, such as low dose gamma radiation, to initiate the formation of the copolymer and the graft/interpenetrating polymerization of the copolymer to the lens material.

In embodiments, a surgical suture, mesh, contact lens, or other medical device may be swollen with a solution containing the furanone possessing vinyl or acrylate groups and the at least one phospholipid possessing at least one vinyl group, optionally in combination with additional vinyl or acrylate monomer. If the device is swollen in a monomer solution utilizing a solvent that does not completely solubilize the monomers, the formation of the resulting copolymer may be localized on the surface of the device and not affect or compromise the bulk properties of the device.

Following polymerization, the device may be removed from the polymerization medium, i.e., the solution containing the monomers and any initiators, catalysts, and the like, and washed to remove excess free copolymer of the present disclosure and/or any residual monomers. The device possessing the copolymer coating, in embodiments grafted and/or interpenetrating, may then be subjected to additional energy treatments, including high energy radiation such as gamma radiation, to both sterilize and further modify the copolymer coating.

In embodiments, a medical device in accordance with the present disclosure may be a suture. Sutures in accordance with the present disclosure may be monofilament or multifilament and may be made of the copolymers of the present disclosure or any conventional material, including both bioabsorbable and non-bioabsorbable materials. Suitable materials include, but are not limited to, surgical gut, silk, cotton, polyolefins such as polypropylene, polyamides, polyglycolic acids, polyesters such as polyethylene terephthalate and glycolide-lactide copolymers, and the like.

In embodiments, the suture may be made of a polyolefin. Suitable polyolefins include polyethylene, polypropylene, copolymers of polyethylene and polypropylene, and blends of polyethylene and polypropylene. In some embodiments, polypropylene can be utilized to form the suture. The polypropylene can be isotactic polypropylene or a mixture of isotactic and syndiotactic or atactic polypropylene.

In other embodiments, the suture may be made from synthetic absorbable polymers such as those made from glycolide, lactide, caprolactone, alkylene carbonates (i.e., trimethylene carbonate, tetramethylene carbonate, and the like), dioxanones, orthoesters, hydroxy alkanoates, hydroxybutyrates, tyrosine carbonates, polymide carbonates, polyimino carbonates such as poly(bisphenol A-iminocarbonate) and poly(hydroquinone-iminocarbonate), and copolymers and combinations thereof. One combination which may be utilized includes glycolide and lactide based polyesters, including copolymers of glycolide and lactide.

As noted above, the suture can be monofilament or multifilament. Where the suture is a monofilament, methods for producing such sutures are within the purview of those skilled in the art. Such methods include forming a suture material, such as a polyolefin resin or a copolymer of the present disclosure, and extruding, drawing and annealing the resin of copolymers to form the monofilament.

Where the sutures are made of multiple filaments, the suture can be made using any technique within the purview of one skilled in the art such as, for example, braiding, weaving or knitting. The filaments may also be combined to produce a non-woven suture. The filaments themselves may be drawn, oriented, crinkled, twisted, commingled or air entangled to form yarns as part of the suture forming process.

In embodiments a multifilament suture of the present disclosure can be produced by braiding. The braiding can be done by any method within the purview of those skilled in the art. For example, braid constructions for sutures and other medical devices are described in U.S. Pat. Nos. 5,019,093, 5,059,213, 5,133,738, 5,181,923, 5,226,912, 5,261,886, 5,306,289, 5,318,575, 5,370,031, 5,383,387, 5,662,682, 5,667,528, and 6,203,564, the entire disclosures of each of which are incorporated by reference herein. Once the suture is constructed, it can be sterilized by any means within the purview of those skilled in the art.

In some cases a tubular braid, or sheath, can be constructed about a core structure which is fed through the center of a braider. Known tubular braided sutures, including those possessing cores, are disclosed, for example, in U.S. Pat. Nos. 3,187,752, 3,565,077, 4,014,973, 4,043,344, and 4,047,533.

In embodiments, a suture in accordance with the present disclosure may be attached to any surgical needle within the purview of those skilled in the art to produce a needled suture. Wounds may be sutured by passing a needled suture through tissue to create wound closure. The needle may then be removed from the suture and the suture tied. The suture may remain in the tissue and help prevent contamination and infection of said tissue by virtue of its antimicrobial properties, thereby promoting wound healing and minimizing infection. The suture coating also advantageously enhances the surgeon's ability to pass the suture through tissue, and increases the ease and security with which he/she can tie the suture.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. An article comprising a coating comprising:
a first monomer comprising at least one vinyl phospholipid monomer; and
a second monomer of formula:

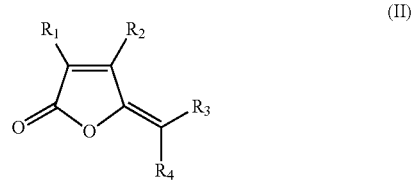

wherein $R_2$, $R_3$ and $R_4$ are independently or all H or halogen; and
$R_1$ is a moiety selected from the group consisting of H, halogen, formyl, carboxyl, cyano, ester, amide, alkyl, alkoxy, oxoalkyl, alkenyl, alkynyl, aryl or arylalkyl,
wherein at least one of $R_1$, $R_2$, $R_3$ and $R_4$ are substituted with a moiety selected from the group consisting of vinyl moieties and acrylate moieties.

2. The article of claim 1, wherein the article is selected from the group consisting of textiles, medical devices, and packaging materials.

3. The article of claim 1, wherein the article comprises a textile formed of fibers made of components selected from the group consisting of natural fibers, synthetic fibers, blends of natural fibers, blends of synthetic fibers, and blends of natural fibers with synthetic fibers.

4. The article of claim 1, wherein the article comprises a textile formed of fibers made of components selected from the group consisting of furanone copolymers, polyesters, polyamides, polyolefins, halogenated polymers, polyester/polyethers, polyurethanes, homopolymers thereof, copolymers thereof, and combinations thereof.

5. The article of claim 1, wherein the article comprises a medical device selected from the group consisting of clips, fasteners, staples, sutures, pins, screws, prosthetic devices, wound dressings, bandages, drug delivery devices, anastomosis rings, surgical blades, contact lenses, intraocular lenses, surgical meshes, stents, grafts, catheters, stent/grafts, knotless wound closures, sealants, adhesives, tissue scaffolds, stapling devices, buttresses, lapbands, orthopedic hardware, pacers, pacemakers, and other implantable devices.

6. The article of claim 1, wherein the article comprises a packaging material for a product selected from the group consisting of medical devices, pharmaceuticals, textiles, consumer goods, and foods.

7. The article of claim 1, wherein the coating is applied as part of a solution including a solvent selected from the group consisting of alcohols, ketones, ethers, aldehydes, acetonitrile, acetic acid, methylene chloride, chloroform, and water.

8. The article of claim 1, wherein the first monomer comprises a phosphorylcholine possessing at least one vinyl group of the formula:

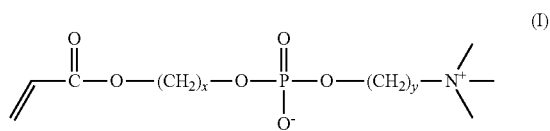

wherein x is from about 1 to about 10, and y is from about 1 to about 10.

9. The article of claim 1, wherein the first monomer is selected from the group consisting of 2-methacryloyloxyethyl phosphorylcholine, 2-acryloyloxyethyl phosphorylcholine and combinations thereof.

10. The article of claim 1, wherein the second monomer comprises a vinyl furanone.

11. The article of claim 1, wherein the article possesses from about 2 to about 8 moles of the second monomer per mole of the first monomer.

12. The article of claim 1, wherein the coating further comprises at least one additional monomer selected from the group consisting of vinyl monomers, acrylate monomers, and combinations thereof.

13. The article of claim 1, wherein the coating further comprises at least one additional monomer selected from the group consisting of vinyl functional quaternary amines, hydroxyethyl methacrylate, n-vinyl pyrrolidone, sodium acrylate, bis-acrylate, styrene sulfonic acid, butyl acrylate, sulfopropyl acrylate, sulfopropyl methacylate, acrylamide, diacrylamide, methacrylic acid, acrylic acid, polyethylene glycol acrylates, polyethylene glycol/polypropylene glycol acrylates, silicone acrylates, and combinations thereof.

14. The article of claim 1, wherein the coating further comprises a fatty acid component selected from the group consisting of fatty acids, fatty acid salts, and salts of fatty acid esters.

15. The article of claim 1, wherein the coating further comprises a component selected from the group consisting of dyes, antimicrobial agents, growth factors, anti-inflammatory agents, and polymer drugs.

16. The article of claim 15, wherein the antimicrobial agent is selected from the group consisting of antibiotics, antiseptics, disinfectants and combinations thereof.

17. The article of claim 15, wherein the antimicrobial agent is selected from the group consisting of minocycline, rifampin, erythromycin, penicillin, nafcillin, cefazolin, imipenem, aztreonam, gentamicin, chloramphenicol, sulfamethoxazole, vancomycin, ciprofloxacin, fusidic acid, trimethoprim, metronidazole, clindamycin, mupirocin, amphotericin B, fluconazole, sulbactam, antimicrobial peptides, antimicrobial proteins, chemotherapeutic drugs, telomerase inhibitors, 5-furanones, mitoxanthone, hexachlorophene, chlorhexidine, cyclohexidine, iodine, povidone-iodine, p-chloro-m-xylenol, triclosan, nitrofurantoin, anitrofurazone, methenamine, glutaraldehyde, formaldehyde, alcohols, and combinations thereof.

18. The article of claim 15, wherein the polymer drug is selected from the group consisting of polymeric antibiotics, polymeric antiseptics, and polymeric non-steroidal anti-inflammatory drugs.

* * * * *